(12) United States Patent
Bandyopadhyay et al.

(10) Patent No.: US 9,717,666 B2
(45) Date of Patent: Aug. 1, 2017

(54) SKIN LIGHTENING COMPOSITION

(75) Inventors: Punam Bandyopadhyay, Bangalore (IN); Sujeetkumar Jha, Dist-Thane (IN); Shilpa Atul Vora, Bangalore (IN); Anita Damodaran, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 7 days.

(21) Appl. No.: 14/115,893

(22) PCT Filed: Apr. 23, 2012

(86) PCT No.: PCT/EP2012/057353
§ 371 (c)(1),
(2), (4) Date: Dec. 3, 2013

(87) PCT Pub. No.: WO2012/152568
PCT Pub. Date: Nov. 15, 2012

(65) Prior Publication Data
US 2014/0086860 A1 Mar. 27, 2014

(30) Foreign Application Priority Data

May 12, 2011 (IN) .......................... 1456/MUM/2011
Aug. 3, 2011 (EP) ...................................... 11176422

(51) Int. Cl.
| A61K 8/365 | (2006.01) |
| A61K 8/362 | (2006.01) |
| A61Q 19/02 | (2006.01) |
| A61K 8/97 | (2017.01) |
| A61K 8/63 | (2006.01) |

(52) U.S. Cl.
CPC .............. *A61K 8/365* (2013.01); *A61K 8/362* (2013.01); *A61K 8/63* (2013.01); *A61K 8/97* (2013.01); *A61Q 19/02* (2013.01)

(58) Field of Classification Search
CPC . A61K 8/97; A61K 8/362; A61K 8/63; A61K 8/356; A61Q 19/02
See application file for complete search history.

(56) References Cited

U.S. PATENT DOCUMENTS

| 4,942,033 | A | * | 7/1990 | Aubert et al. | ................. 424/745 |
| 5,296,157 | A | * | 3/1994 | MacGilp et al. | ............. 510/140 |
| 7,332,152 | B2 | | 2/2008 | Sanzgiri | |
| 2001/0029266 | A1 | | 10/2001 | Leroy | |
| 2007/0134167 | A2 | | 6/2007 | Neubourg | |
| 2008/0160110 | A1 | | 7/2008 | Kang | |

FOREIGN PATENT DOCUMENTS

| CN | 1611207 | | 5/2005 |
| CN | 1611207 | A * | 5/2005 |
| CN | 1723009 | | 1/2008 |
| DE | 19857492 | | 6/2000 |
| DE | 19857492 | A1 | 6/2000 |
| EP | 958808 | | 11/1999 |
| FR | 2541895 | | 9/1984 |
| FR | 2541895 | | 8/1985 |
| JP | 04018017 | | 1/1992 |
| JP | 11029467 | | 2/1999 |
| JP | 2001163755 | | 6/2001 |
| JP | 2002241299 | | 8/2002 |
| JP | 2007332066 | | 12/2007 |
| JP | 2010030927 | | 2/2010 |
| JP | 2011068572 | | 4/2011 |
| KR | 20050092313 | | 9/2005 |
| WO | WO0064279 | | 11/2000 |
| WO | WO 2004096171 | A1 * | 11/2004 |
| WO | WO 2006088385 | A2 * | 8/2006 |
| WO | WO 2008104591 | A2 * | 9/2008 |

OTHER PUBLICATIONS

FooDB "Sodium Fumarate." Retrieved on May 12, 2015. Retrieved from the internet <URL: http://foodb.ca/compounds/FDB017286>.*
Shueller "Stearic acid." Retrieved on May 12, 2015. Retrieved from the internet <URL: http://science.jrank.org/pages/6482/Stearic-Acid.html>.*
Prospector "Brij™ S10." Retrieved on May 12, 2015. Retrieved from the internet <URL: https://www.ulprospector.com/en/na/PersonalCare/Detail/134/22370/Brij-S10>.*
Godrej Industries Limited—"Hystric—Triple Pressed Stearic Acid." Retrieved on Mar. 15, 2016. Retrieved from the internet <URL: http://www.godrejindustries.com/Resources/pdf/chemicals/fatty-acids/stearic-acids/cosmetic-grade/hystric_triple_pressed_stearic_acid.pdf>.*
Zauba Corp—"Details of HY-STRIC trademark." Retrieved on Mar. 15, 2016. Retrieved from the Internet <URL: https://www.zaubacorp.com/trademark/HY-STRIC/580338>.*
English Translation of CN1611207A from Google Patent. Accessed on Aug. 4, 2016.*
IPRP1 in PCTEP2012057352 dated Nov. 12, 2013.
IPRP1 in PCTEP2012057353 dated Nov. 12, 2013.
Written Opinion in EP11176422 dated Jan. 16, 2012.
PCT International Search Report in PCT application PCT/EP2012/057353 dated Jul. 26, 2013 with Written Opinion.
European Search Report in EP application EP 11 17 7301 dated Jan. 25, 2012 with Written Opinion.
PCT International Search Report in PCT application PCT/EP2012/057352 dated Jul. 26, 2013 with Written Opinion.

(Continued)

*Primary Examiner* — Anoop Singh
*Assistant Examiner* — Doan Phan
(74) *Attorney, Agent, or Firm* — Greenberg Traurig, LLP

(57) ABSTRACT

The invention relates to a skin lightening composition, more particularly a composition which derives synergy between an active of natural origin and an active of synthetic origin. The present inventors have judiciously combined a selective salt of a dicarboxylic acid viz. disodium fumarate along with a specific extract of a plant source e.g. *Salvia officinalis* rich in certain organic aromatic acids to provide for synergic skin lightening benefits. They have further found that inclusion of certain activity enhancers in the composition of the invention improves the skin lightening efficacy.

3 Claims, No Drawings

(56) References Cited

OTHER PUBLICATIONS

European Search Report in EP application EP 11 17 6422 dated Jan. 16, 2012.
Saniya Salihova, Clarifying and bleaching masks: Sage, Treatment by herbs, 2006, pp. 1-14 (with English human translation of Section 3.2, first paragraph only).

* cited by examiner

SKIN LIGHTENING COMPOSITION

FIELD OF THE INVENTION

The invention relates to a skin lightening composition. The invention more particularly relates to a skin lightening composition which derives synergy between an active of natural origin and an active of synthetic origin.

BACKGROUND OF THE INVENTION

Highly pleasing skin appearance is one of the most desired expectations from personal care products from most consumers around the world. In tropical countries where consumers generally have dark skin, there is a desire to have lighter skin appearance. In consumers who live far from the tropical countries e.g. the Caucasian people who generally have lighter skin, there is a problem of freckles and hyper pigmentation when they are exposed to bright sunshine and therefore they desire an even tanned tone of their skin. Most consumers experience blemishes on their skin after exposure to sun, on healing of wounds or after drying up of acne. In all of the above cases, consumers rely on cosmetic solutions to their skin appearance problems.

Smooth, soft and glowing skin with even skin tone and colour is thus desired by all consumers who use personal care compositions for their skin. To provide this benefit, manufacturers from around the world have tried many approaches. One very commonly used approach is to include sunscreens or sunblocks in such cosmetic products. Another approach to controlling the colour, tone and appearance of the skin is the so called skin lightening approach where chemical compounds are added to personal care compositions which alter the formation of melanin in the skin through biochemical transformation in the stratum corneum thereby changing the colour and appearance of the skin. There are many reactions, some in parallel and some occurring in series which finally affect the formation of melanin in the skin. Different compounds work through different mechanisms. The present inventors have realized over the course of several years of research in this area that there are both advantages and disadvantages of chemical compounds derived from natural source and from those of synthetic origin. The present inventors have judiciously combined one active from each of the natural and synthetic sources in order to get synergistic benefits while minimizing the disadvantage of each type and have thus come up with the present invention. They have found that combination of a selective salt of a dicarboxylic acid viz. disodium fumarate along with a specific extract of a plant source e.g. *Salvia officinalis* rich in certain organic aromatic acids provides for synergic skin lightening benefits. They have further found that inclusion of certain activity enhancers in the composition of the invention improves the skin lightening efficacy.

U.S. Pat. No. 7,332,152 discloses a cosmetic composition comprising vitamin B6, vitamin B3 and an organic acid that interact synergistically to enhance skin lightening. JP 418017 discloses a sebum secretion promoting agent which is made by selecting one or more compounds selected from citric acid, succinic acid, fumaric acid, malic acid or an ester thereof and an extracted solution of *Salvia officinalis* L. with ethanol.

JP 2001 163755 discloses a preparation for external use for skin for improved skin bleaching effect, excellent in stability and safety by including at least one plant extract selected from those derived from *Morus alba, Scutellaria baicalensis, Rosamarinus officinalis, Matricaria chamomilla, Aloe ferox* (or *Aloe africane, Aloe spicata, Aloe barbadensis* or *Aloe arborescens*), *Hamamelis virginiana, Aesculus hippocastanum, Rosa multiflora* or species closely related thereto (Rosaceae), *Salvia officinalis, Lamium album, Isodon japonicus* (or *Isodon trichocarpus*), *Glycyrrhiza glabra* (or *Glycyrrhiza uralensis*), *Saxifraga stolonfera, Rosa centigolia,* and/or *Pyracantha fortuneana,* and an acylated derivative of glycosyl-L-ascorbic acid.

Thus no published information exists that specifically teaches synergistic interaction of disodium fumarate with an extract of plant source like *Salvia officinalis* to provide enhanced skin lightening benefits.

It is an object of the present invention to provide for a skin lightening composition that exhibits enhanced skin lightening as compared to known products available in the market.

It is another object of the present invention to provide for enhanced skin lightening composition using specific actives extracted from both a natural source and a synthetic source.

SUMMARY OF THE INVENTION

The present invention provides for a skin lightening composition comprising,
a) 0.1 to 5% by weight disodium fumarate;
b) 0.01 to 5% by weight an extract of a plant material comprising 50 to 100% ursolic acid; and
c) a cosmetically acceptable vehicle.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. The disclosure of the invention as found herein is to be considered to cover all embodiments as found in the claims as being multiply dependent upon each other irrespective of the fact that claims may be found without multiple dependency or redundancy.

"Skin lightening composition" as used herein, is meant to include a composition for topical application to skin of mammals, especially humans. Such a composition may be generally classified as leave-on or rinse off preferably leave-on. It includes any product applied to a human body primarily for lightening the colour of the skin but may also provide improved appearance, cleansing, odor control, photoprotection or general aesthetics. They may also be incorporated in compositions which are primarily meant as antiperspirants, deodorants, depilatories, lipsticks, foundations, mascara, sunscreen lotions, shampoos, or conditioners but provide additional benefits of skin lightening. "Skin" as used herein is meant to include skin on the face and body (e.g., neck, chest, back, arms, underarms, hands, legs, buttocks and scalp).

The composition of the present invention is primarily targeted to skin lightening applications. The inventors have surprisingly found that in addition to providing the skin lightening benefit, advantages like anti-aging and relief from photo damage are also provided.

The composition of the present invention is preferably in the form of a cream, lotion, stick, gel, roll-on or in propellant containing aerosol form. They are preferably in the cream, lotion, gel or stick form, most preferably in cream form.

The skin lightening composition of the invention comprises a selective salt of dicarboxylic acid (disodium fumarate), a specific extract of a plant source and a cosmetically acceptable vehicle.

Disodium fumarate has the structure as shown below

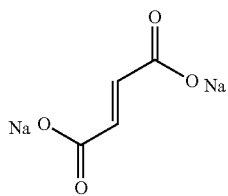

Disodium fumarate is present in 0.1 to 5%, preferably 0.2 to 3%, further more preferably 0.5 to 2% by weight of the composition.

The composition of the invention comprises 0.01 to 5%, preferably 0.1 to 5% by weight an extract of a plant material comprising 50 to 100% ursolic acid. The extract of plant material preferably additionally comprises 0.1 to 50% oleonolic acid.

Ursolic acid and oleonolic acid have the structure given below:

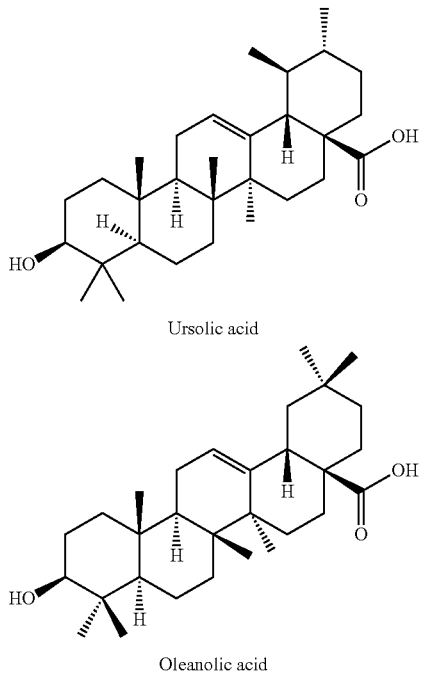

Ursolic acid

Oleanolic acid

The plant material for providing the extract used in this invention is preferably *Salvia officinalis*.

*Salvia officinalis* is often referred to by the common name of Garden sage or Common sage. It is a small perennial evergreen subshrub, with woody stems, grayish leaves, and blue to purplish flowers. It is a member of the family Lamiaceae and is native to the Mediterranean region. It is cultivated in many European countries and in North America. It has been used in medicinal preparations and in foods. In the present invention, the leaves and soft stems of *Salvia officinalis* are used for extracting the desired actives, preferably the leaves. Sage leaf contains the following chemical class of compounds: catechin-type tannins, phenolic acids, flavonoids, essential oil and triterpenoids which includes oleanolic and ursolic acids.

A preferred process of extracting the extract of the plant material comprising 0.1 to 100% ursolic acid for use in the composition of the invention is prepared using a process comprising the steps of (a) contacting the plant material Saliva officinalis with a non-polar solvent selected from hexane, ethyl acetate, toluene, chloroform, diethyl ether or methylene chloride to prepare a mixture; and (b) separating the solvent from the mixture to prepare the extract. The separation of the solvent may be carried out by any known method. A preferred method is evaporation of the solvent under vacuum, preferably followed by filtration, washing and drying to a powder.

The extract may be further purified by a step of washing the extract with a solvent which may be hexane, acetone or a mixture thereof. Further purification steps may involve dissolving the extract in a basic solution e.g. alkaline ammonia followed by filtering the solution free of insoluble material and neutralizing the solution with acid to a neutral pH to precipitate the desired extract which may be further washed with distilled water and dried to a powder which contains ursolic acid.

The plant extract comprises 50 to 100% ursolic acid, preferably 60 to 95%, further preferably 60 to 85% ursolic acid. A preferred aspect provides oleonolic acid to be present in 15 to 40% by weight of the plant extract. In a highly preferred aspect, both ursolic acid and oleonolic acid are present. By the term extract is meant a product in dry form which could be in powder, granule or in the form of lumps. The percentage of fatty acid in the extract of plant material throughout this specification, unless mentioned otherwise, is on dry weight basis.

The composition of the invention comprises a cosmetically acceptable vehicle. The cosmetically acceptable vehicle preferably comprises 1 to 25% fatty acid. The cosmetically acceptable vehicles are preferably in a cream, lotion, gel or emulsion format. A more preferred format is a cream, further more preferably a vanishing cream. Vanishing cream base is one which comprises 1 to 25%, more preferably 5 to 20% fatty acid. The base preferably comprises 0.1 to 10%, more preferably 0.1 to 3% soap. $C_{12}$ to $C_{20}$ fatty acids are especially preferred in vanishing cream bases, further more preferred being $C_{14}$ to $C_{18}$ fatty acids. In creams, the fatty acid is preferably substantially a mixture of stearic acid and palmitic acid. Soaps in the vanishing cream base include alkali metal salt of fatty acids, like sodium or potassium salts The soap is preferably the potassium salt of the fatty acid mixture. The fatty acid in vanishing cream base is often prepared using hystric acid which is substantially (generally about 90 to 95%) a mixture of stearic acid and palmitic acid. Thus, inclusion of hystric acid and its soap to prepare the vanishing cream base is within the scope of the present invention. It is particularly preferred that the composition comprises at least 6%, preferably at least 10%, more preferably at least 12% fatty acid. The cosmetically acceptable vehicle is usually from 10 to 99.9%, preferably from 50 to 99% by weight of the composition. The cosmetically acceptable vehicle preferably includes water. Water is preferably included in 35 to 90%, more preferably 50 to 85%, further more preferably 50 to 80% by weight of the composition.

The composition of the invention preferably comprises an activity enhancer selected from an organic base. By the term organic base is meant that a compound which contains the functional groups —NH2, —NHR or —NR2, (where R may be alkyl or aryl) and gives a pH of about 10 to 12 in water at 1% concentration. A preferred organic base is an amine compound. Preferred amine compounds include alkanol amines like monoethanol amine, di ethanolamines, triethanol amine and alkyl amines like methylamine, ethylamine, dimethyl amine, diethyl amine, dimethylethyl amine and triethyl amine. Amines are preferably present in 0.05 to 5%, more preferably 0.1 to 2.5% by weight of the composition.

The composition of the invention preferably comprises an additional activity enhancer selected from polyhydric alcohols. Polyhydric alcohols useful for inclusion in the composition of the invention may be selected from alkylene glycols and/or polyalkylene glycols. Examples of polyhydric alcohols useful in the composition of the invention are ethylene glycol, diethylene glycol, triethylene glycol, tetraethylene glycol, polyethylene glycols, propylene glycol, butanediol, pentanediol, hexanediol, glycerol or phytantriol When included polyhydric alcohols are present in 0.01 to 10%, preferably 0.1 to 5% by weight of the composition.

A highly preferred aspect of the invention comprises an activity enhancer selected from organic amines, polyhydric alcohols or mixtures thereof. Suitable ratio of amine and polyhydric alcohol is in the range of 1:1 to 1:5. Total amount of activity enhancer is preferably in the range of 1 to 10% by weight of the composition. Most preferred organic amine is triethanol amine. Most preferred polyhydric alcohol is propylene glycol. Not wishing to be bound by theory it has been found that depending on the activity enhancer being used, they act through different mechanisms including enhanced solubility of the organic aromatic acids present in the plant extract, providing enhanced transdermal delivery of the primary skin lightening actives or a combination of the two to provide overall enhanced skin lightening.

The composition preferably comprises a non-ionic surfactant. Non-ionic surfactant has also been seen to be a skin lightening activity enhancer in certain cases, in addition to its known properties. In addition to the mechanism of action of the other activity enhancer hereinabove described, non-ionic surfactants enable enhancement of skin lightening activity, in the present invention, by way of improving spreading of the formulation on the skin where it is applied. The non-ionic surfactant may be present in 0.01 to 10%, preferably 0.1 to 5%, more preferably 0.1 to 3% by weight of the composition. Preferred non-ionic surfactants are those that have an HLB value of at least 9.0

The non-ionic surfactants suitable for inclusion in the composition of the invention are
(i) fatty alcohol ethoxylates with saturated carbon chain and having HLB greater than 15 or
(ii) fatty alcohol ethoxylates with unsaturated carbon chain with HLB greater than 12; or
(iii) alkyl phenol ethoxylate; or
(iv) polyoxyethylene sorbitan mono alkyl esters having carbon chain length 12 to 16 and having an HLB value greater than 12 or
(v) polyoxyethylene sorbitan mono alkyl esters of unsaturated $C_{18}$ and having an HLB value greater than 12.

Of the above, the classes (i) and (ii) are generally known as the Brij surfactants, the class (iii) is generally known as the Triton class and the classes (iv) and (v) are called the Tween class.

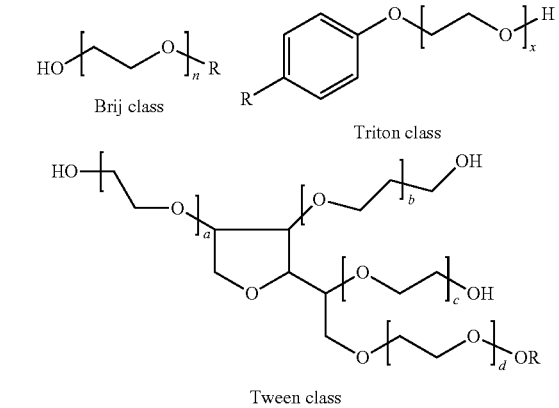

Where R=long carbon chain

Suitable examples of (a) fatty alcohol ethoxylates with saturated carbon chain and having HLB higher than 15.5 or from (b) the class of fatty alcohol ethoxylates with unsaturated carbon chain with HLB higher than 12 are Brij 35 (a C12EO23 compound), Brij 97 (unsaturated C18EO12), Brij 700 (C18EO100) or Brij 99 (unsaturated C18EO20). Suitable examples of (c) alkyl phenol ethoxylates with HLB higher than 15 for use in the composition of the invention are Triton X 165, Triton X 305, Triton 405, or Triton X 705. Suitable examples of (d) polyoxyethylene sorbitan alkyl esters with saturated C12 to C16 carbon chain and having HLB higher than 12 and (e) polyoxyethylene sorbitan alkyl esters with unsaturated C18 carbon chain and having HLB higher than 9 are Tween 20, Tween 21, Tween 40, Tween 80, Tween 81 or Tween 85 trioleate.

It is preferred that the composition of the invention has a pH in the range of 6 to 8.

The composition of the invention may additionally comprise another skin lightening agent. The skin lightening agent is preferably chosen from a vitamin B3 compound or its derivative e.g. niacin, nicotinic acid, niacinamide. Other well known skin lightening agents which may be included are aloe extract, ammonium lactate, azelaic acid, kojic acid, butyl hydroxy anisole, butyl hydroxy toluene, citrate esters, 2,5-dihydroxybenzoic acid and its derivatives, ellagic acid, gluconic acid, glycolic acid, green tea extract, hydroquinone, 4-hydroxy benzoic acid derivatives, hydroxycaprylic acid, lemon extract, linoleic acid, magnesium ascorbyl phosphate, salicylic acid, or vitamins like vitamin B6, vitamin B12, vitamin C, vitamin A, hydroxycarboxylic acid like lactic acid and their salts e.g. sodium lactate, and mixtures thereof. Vitamin B3 compound or its derivative e.g. niacin, nicotinic acid, niacinamide are the more preferred additional skin lightening agent as per the invention, most preferred being niacinamide. Additional skin lightening agent, when included, is preferably present in an amount in the range of 0.1 to 10%, more preferably 0.2 to 5% by weight of the composition.

The personal care composition may preferably additionally comprise one or more UV sunscreens. The UV sunscreens may be inorganic or organic.

A wide variety of organic sunscreen agents are suitable for use in combination with the essential ingredients of this invention. Suitable UV-A/UV-B sunscreen agents include, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))amin-obenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, 2-ethylhexyl-p-methoxycinnamate, butylmethoxydibenzoylmethane, 2-hydroxy-4-methoxybenzophenone, octyldimethyl-p-aminobenzoic acid and mixtures thereof. Most suitable organic sunscreen are 2-ethylhexyl-p-methoxycinnamate and butylmethoxydibenzoylmethane.

A safe and effective amount of sunscreen may be used in the compositions of the present invention. The composition preferably comprises from about 0.1 to about 10%, more preferably from about 0.1 to about 5%, of a sunscreen agent.

Useful inorganic sun-blocks are also preferably used in the present invention. These include, for example, zinc oxide iron oxide, silica, such as fumed silica, and titanium dioxide.

The composition of the invention may additionally comprise deodorant actives for preparation of a deodourant composition which by way of the invention provides fast kinetics of skin lightening. Deodorant compositions are applied on many areas of the human body but are especially popular for use in the axilla or the underarm area. Deodorant compositions can generally be in the form of firm solids, soft solids, gels, creams, liquids, or sprays and are dispensed using applicators appropriate to the physical characteristics of the composition. For the purposes of the present invention, the composition is preferably in the cream format. Deodourant compositions may or may not additionally comprise anti-perspirant actives.

The composition according to the invention may also comprise other diluents. The diluents act as a dispersant or carrier for other materials present in the composition, so as to facilitate their distribution when the composition is applied to the skin.

Diluents other than water can include liquid or solid emollients, solvents, humectants, thickeners and powders.

The cosmetically acceptable vehicle is usually from 10 to 99.9%, preferably from 50 to 99% by weight of the composition, and can, in the absence of other cosmetic adjuncts, form the balance of the composition.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

Source and Geographical Origin of Biological Materials:

The extract of *Salvia officinalis* was sourced from Sami Labs, Bangalore, India who procured the plant material from Africa.

The invention is now further described by way of the following non-limiting examples.

EXAMPLES

Examples 1 to 5: Skin Lightening Efficacy of Compositions Demonstrating Synergy of the Skin Lightening Actives of the Invention Compositions as shown in table 1 were prepared and the skin lightening efficacy was tested using the (MRIV) protocol as described below.

Protocol: A trial was carried out for 10 days with 15 volunteers. The trial consisted of the procedure as described below:

A specific portion of the volunteer's forearm was marked out and formulations were applied (3 mg/cm$^2$) five times daily in about equal intervals of time. The skin lightening score was measured by expert assessors using a colour ruler on a scale of 1 to 10. The data in table 1 below summarizes the average skin lightening score that is the change in skin colour with respect to the initial skin colour. A more negative score indicates a higher degree of skin lightening. A more positive score indicates skin darkening.

The skin lightening efficacy of the compositions at the end of 10 days is also summarized in table 1 below.

TABLE 1

| Ingredients | Example 1 wt % | Example 2 wt % | Example 3 wt % | Example 4 wt % | Example 5 wt % |
| --- | --- | --- | --- | --- | --- |
| Hystric Acid | 17 | 17 | 17 | 17 | 17 |
| Extract of *Salvia officinalis** | — | 1.00 | — | 0.50 | 0.25 |
| Disodium fumarate | — | — | 1.00 | 0.50 | 0.50 |
| Triethanol amine | — | — | — | — | 2.5 |
| Propylene glycol | | | | | 5.0 |
| Non-ionic surfactant, Brij-35 | — | — | — | — | 0.25 |
| Tween-80 | | | | | 0.50 |
| Potassium hydroxide | 0.57 | 0.57 | 0.57 | 0.57 | 0.57 |
| Silicone oil | 0.5 | 0.5 | 0.5 | 0.5 | 0.5 |
| Perfume | 0.3 | 0.3 | 0.3 | 0.3 | 0.3 |
| Methyl paraben + propyl paraben | 0.3 | 0.3 | 0.3 | 0.3 | 0.3 |
| Water | To 100 | To 100 | To 100 | To 100 | To 100 |
| Skin lightening score (day 10) | −0.177 | −0.177 | −0.184 | −0.229 | −0.295 |

*In the compositions shown in table 1, the extract of *Salvia officinalis* had 64% ursolic acid and 21% oleonolic acid.

The data in table 1 indicates that composition as per the invention (examples 4) provides for vastly improved skin lightening efficacy as compared to compositions outside the invention (examples 2 and 3) and a conventional cosmetically acceptable base without any skin lightening active (example 1). Further, inclusion of activity enhancers (example 5) further improves the skin lightening efficacy.

The invention claimed is:

1. A skin lightening composition comprising:

a) 0.5% by weight disodium fumarate;

b) 0.25 to 0.5% by weight an extract of *Salvia officinalis*;

c) 6 to 17% by weight of a mixture of stearic acid and palmitic acid; and d) a cosmetically acceptable vehicle.

2. A composition as claimed in claim 1 wherein the cosmetically acceptable vehicle comprises 1 to 25% by weight fatty acid.

3. A composition as claimed in claim 1 having a pH in the range of 6 to 8.

\* \* \* \* \*